(12) United States Patent
Dorok et al.

(10) Patent No.: US 10,374,165 B2
(45) Date of Patent: Aug. 6, 2019

(54) ORGANIC ELECTRONIC DEVICE

(71) Applicant: Novaled GmbH, Dresden (DE)

(72) Inventors: Sascha Dorok, Dresden (DE); Carsten Rothe, Dresden (DE); Omrane Fadhel, Dresden (DE); Francois Cardinali, Dresden (DE)

(73) Assignee: Novaled GmbH, Dresden (DE)

( * ) Notice: Subject to any disclaimer, the term of this patent is extended or adjusted under 35 U.S.C. 154(b) by 908 days.

(21) Appl. No.: 14/361,664

(22) PCT Filed: Nov. 30, 2012

(86) PCT No.: PCT/EP2012/074127
§ 371 (c)(1),
(2) Date: May 29, 2014

(87) PCT Pub. No.: WO2013/079678
PCT Pub. Date: Jun. 6, 2013

(65) Prior Publication Data
US 2014/0353649 A1    Dec. 4, 2014

(30) Foreign Application Priority Data

Nov. 30, 2011  (EP) .................................. 11191351

(51) Int. Cl.
| | |
|---|---|
| *H01L 51/00* | (2006.01) |
| *H01L 51/50* | (2006.01) |
| *C09K 11/06* | (2006.01) |
| *C07F 9/53* | (2006.01) |
| *C07F 9/576* | (2006.01) |
| *H01L 51/44* | (2006.01) |
| *H01L 51/05* | (2006.01) |
| *H01L 51/52* | (2006.01) |

(52) U.S. Cl.
CPC ........ *H01L 51/0062* (2013.01); *C07F 9/5325* (2013.01); *C07F 9/5765* (2013.01); *C09K 11/06* (2013.01); *H01L 51/005* (2013.01); *H01L 51/0072* (2013.01); *H01L 51/0077* (2013.01); *H01L 51/44* (2013.01); *H01L 51/5092* (2013.01); *C09K 2211/181* (2013.01); *H01L 51/0512* (2013.01); *H01L 51/5072* (2013.01); *H01L 51/52* (2013.01); *Y02E 10/549* (2013.01)

(58) Field of Classification Search
CPC .............. H01L 51/0062; H01L 51/005; H01L 51/0072; H01L 51/0077; H01L 51/44; H01L 51/5092; H01L 51/0512; H01L 51/5072; H01L 51/52; C07F 9/5325; C07F 9/5765; C09K 11/06; C09K 2211/181; Y02E 10/549
See application file for complete search history.

(56) References Cited

U.S. PATENT DOCUMENTS

| | | |
|---|---|---|
| 6,013,384 A | 1/2000 | Kido et al. |
| 6,589,673 B1 | 7/2003 | Kido et al. |
| 7,074,500 B2 | 7/2006 | Pfeiffer et al. |
| 2007/0018154 A1 | 1/2007 | Bae et al. |
| 2007/0029065 A1 | 2/2007 | Takahashi et al. |
| 2007/0138950 A1 | 6/2007 | Yamamoto et al. |
| 2007/0196688 A1 | 8/2007 | Ikeda et al. |
| 2007/0222373 A1 | 9/2007 | Arakane et al. |
| 2007/0267970 A1 | 11/2007 | Yamamoto et al. |
| 2008/0111473 A1 | 5/2008 | Kawamura et al. |
| 2008/0227979 A1 | 9/2008 | Saalbeck et al. |
| 2008/0284325 A1 | 11/2008 | Noh et al. |
| 2009/0212280 A1 | 8/2009 | Werner et al. |
| 2009/0217963 A1 | 9/2009 | Pfeiffer et al. |
| 2009/0235971 A1 | 9/2009 | Pfeiffer et al. |
| 2009/0278115 A1 | 11/2009 | Hosokawa et al. |
| 2010/0123390 A1 | 5/2010 | Kamatani et al. |
| 2010/0157131 A1 | 6/2010 | Kamatani et al. |

FOREIGN PATENT DOCUMENTS

| | | |
|---|---|---|
| JP | 2002-063989 A | 2/2002 |
| JP | 2003-031370 A | 1/2003 |
| JP | 2004-203828 A | 7/2004 |

(Continued)

OTHER PUBLICATIONS

Ha et al. (Applied Physics Letters (2008), 93, 043306, p. 1-3).*
Pu et al. (Organic Electronics, 10 (2009), p. 228-232).*
Machine Translation of Yu et al. (JP JP2008270729) (2008).*
Machine Translation of Junji et al. (JP2008195623) (2008).*
Japanese Office Action for JP Application No. 2014-543921 dated Oct. 4, 2016 (English translation) (3 pages).
Chinese Office Action for CN Application No. 201280067205.0 dated Apr. 29, 2016 (5 pages).
Chou et al., "A Highly Efficient Universal Bipolar Host for Blue, Green, and Red Phosphorescent OLEDs," Adv. Mater., 2010, 22:2468-2471.

(Continued)

Primary Examiner — Robert H Havlin
(74) Attorney, Agent, or Firm — Eversheds Sutherland (US) LLP

(57) ABSTRACT

The present invention relates to an organic electronic device, comprising a first electrode, a second electrode, and a substantially organic layer comprising a compound according to formula (I) between the first and the second electrode:

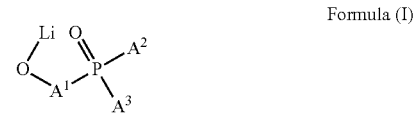

Formula (I)

wherein $A^1$ is a C6-C20 arylene and each of $A^2$-$A^3$ is independently selected from a C6-C20 aryl, wherein the aryl or arylene may be unsubstituted or substituted with groups comprising C and H or with a further LiO group, provided that the given C count in an aryl or arylene group includes also all substituents present on the said group.

11 Claims, 1 Drawing Sheet

(56) References Cited

FOREIGN PATENT DOCUMENTS

| | | | |
|---|---|---|---|
| JP | 2004-204140 A | 7/2004 | |
| JP | 2008-106180 A | 5/2008 | |
| JP | 2008-195623 A | 8/2008 | |
| JP | 2008-270729 A | 11/2008 | |
| KR | 10-2007-0095042 A | 9/2007 | |
| WO | 03/088271 A1 | 10/2003 | |
| WO | WO 2009149860 * | 12/2009 | ............. H01L 51/00 |
| WO | 2011/010656 A1 | 1/2011 | |
| WO | 2011/154131 A1 | 12/2011 | |

OTHER PUBLICATIONS

Pu et al., "Lithium Phenolate Complexes for an Electron Injection Layer in Organic Light-Emitting Diodes," Organic Electronics, 2009, 10(2):228-232.

Taiwanese Office Action for TW Application No. 101145001 dated Apr. 20, 2016 (3 pages) (English Translation).

PCT International Search Report for PCT Application No. PCT/EP2012/074127 dated Mar. 1, 2013 (1 page).

Ha et al., "Low Voltage Organic Light-Emitting Devices with Triphenylphosphine Oxide Layer," Applied Physics Letters, 2008, 93:043306-1-3.

Lee et al., "Effects of Hydroxyl Groups in Polymeric Dielectrics on Organic Transistor Performance," Applied Physics Letters, 2006, 88:162109-1-3.

Matsushima et al., "Extremely Low Voltage Organic Light-Emitting Diodes with p-Doped Alpha-Sexithiophene Hole Transport and n-Doped Phenyldipyrenylphosphine Oxide Electron Transport Layers," Applied Physics Letters, 2006, 253506-1-3.

Korean Office Action for KR Application No. 10-2014-7018175 dated Jan. 18, 2019 (English translation) (5 pages).

* cited by examiner

ORGANIC ELECTRONIC DEVICE

CROSS-REFERENCE TO RELATED APPLICATIONS

This is a submission pursuant to 35 U.S.C. 154(d)(4) to enter the national stage under 35 U.S.C. 371 for PCT/EP2012/074127, filed Nov. 30, 2012. Priority is claimed under 35 U.S.C. 119(a) and 35 U.S.C. 365(b) to European Application No. 11 191 351.3, filed Nov. 30, 2011. The subject matters of PCT/EP2012/074127 and European Application No. 11 191 351.3 are incorporated herein by reference.

FIELD OF THE INVENTION

The present invention relates to an organic electronic device and to a use of a specific compound in such an organic electronic device.

BACKGROUND

Organic electronic devices, such as organic semiconductors, can be used to fabricate simple electronic components, e.g. resistors, diodes, field effect transistors, and also optoelectronic components like organic light emitting devices (e.g. organic light emitting diodes (OLED)), and many others. The industrial and economical significance of the organic semiconductors and their devices is reflected in the increased number of devices using organic semiconducting active layers and the increasing industry focus on the subject.

OLEDs are based on the principle of electroluminescence in which electron-hole pairs, so-called excitons, recombine under the emission of light. To this end the OLED is constructed in the form of a sandwich structure wherein at least one organic film is arranged as active material between two electrodes, positive and negative charge carriers are injected into the organic material and a charge transport takes place from holes or electrons to a recombination zone (light emitting layer) in the organic layer where a recombination of the charge carrier to singlet and/or triplet excitons occurs under the emission of light. The subsequent radiant recombination of excitons causes the emission of the visible useful light emitted by the light-emitting diode. In order that this light can leave the component at least one of the electrodes must be transparent. Typically, a transparent electrode consists of conductive oxides designated as TCOs (transparent conductive oxides), or a very thin metal electrode; however other materials can be used. The starting point in the manufacture of an OLED is a substrate on which the individual layers of the OLED are applied. If the electrode nearest to the substrate is transparent the component is designated as a "bottom-emitting OLED" and if the other electrode is designed to be transparent the component is designated as a "top-emitting OLED". The layers of the OLEDs can comprise small molecules, polymers, or be hybrid.

Several operational parameters of the OLED are being constantly improved to enhance the overall power efficiency. One important parameter is the operation voltage which can be tuned by improving the transport of charge carriers and/or reducing energy barriers such as the injection barriers from the electrodes, another important figure is the quantum efficiency, and also very relevant is the lifetime of the device. Other organic devices, such as organic solar cells also require improving in efficiency, which nowadays, are at best at about 9%.

Like an OLED, an organic solar cell has a stack of organic layers between two electrodes. In a solar cell, there must be at least one organic layer responsible for the absorption of light and a interface which separates the excitons created by the absorption (photo-active). The interface can be a bi-layer heterojunction, a bulk-heterojunction, or can comprise more layers, e.g., in a step wise interface. Also sensitizing layers and others can be provided. For increased efficiency, a good charge carrier transport is required, in some device structures the transport regions must not absorb light, therefore transport layers and photo-active layers may comprise different materials. Also charge carrier and/or exciton blocking layers may be employed. Highest efficiency solar-cells are, nowadays, multi-layer solar cells, some device structures are stacked (multi-junction solar cells) and connected by a connecting unit (also called recombination layer); nevertheless, single junction solar cells could have a high performance if the right materials were found. Examples of devices are given in US2009217980, or in US2009235971.

Differently than OLEDs and organic solar cells, transistors do not require doping of the entire semiconducting (channel) layer, because the concentration of available charge carriers is determined by an electric field supplied by a third electrode (gate electrode). However, convention organic thin film transistors (OTFTs) require very high voltages to operate. There is a need to lower this operating voltage; such an optimization can be done, e.g. with appropriate injection layers.

Organic transistors are also called organic field-effect transistors. It is anticipated that a large number of OTFTs can be used for example in inexpensive integrated circuits for non-contact identification tags (RFID) but also for screen control. In order to achieve inexpensive applications, generally thin-layer processes are required to manufacture the transistors. In recent years performance features have been improved to such an extent that the commercialization of organic transistors is foreseeable. For example, in OTFTs high field-effect mobilities of up to 5.5 cm2/Vs for holes on the basis of pentacene (Lee et al., Appl. Lett. 88, 162109 (2006)) have been reported. A typical organic field-effect transistor comprises an active layer of organic semiconducting material (semiconducting layer) material which during the operation forms an electrical conduction channel, a drain and a source electrodes which exchange electrical charges with the semiconducting layer, and a gate electrode which is electrically isolated from the semiconducting layer by an dielectric layer.

There is a clear need to improve charge carrier injection and/or conductivity in organic electronic devices. Reducing or eliminating the barrier for charge injection between the electrode and the electron transport material (ETM) contributes strongly to enhancement of the device efficiency. Nowadays, there are two main approaches to reduce voltage and enhance efficiencies of organic electronic devices: improvement of the charge carrier injection and improvement of the conductivity of the transport layers. Both approaches can be used in combination.

For instance, U.S. Pat. No. 7,074,500 discloses a component structure for an OLED which leads to a greatly improved charge carrier injection from the electrodes into the organic layers. This effect is based on considerable band bending of the energy levels in the organic layer at the interface to the electrodes, as a result of which injection of charge carriers on the basis of a tunnel mechanism is possible. The high conductivity of the doped layers also prevents the voltage drop which occurs there during operation of the OLED. The injection barriers which may occur in OLEDs between the electrodes and the charge carrier transport layers are one of the main causes for an increase in the operating voltage compared to the thermodynamically justified minimum operating voltages. For this reason, many attempts have been made to reduce the injection barriers, for example by using cathode materials with a low work function, for example metals such as calcium or barium. However, these materials are highly reactive, difficult to process and are only suitable to a limited extent as electrode materials. Moreover, any reduction in operating voltage brought about by using such cathodes is only partial.

Metals having low work function, in particular alkali metals such as Li and Cs, are often used either as the cathode material or the injection layer to promote electron injection. They have also widely been used as dopants in order to increase the conductivity of the ETM, U.S. Pat. Nos. 6,013,384, 6,589,673. Metals such as Li or Cs provide a high conductivity in matrixes which are difficult to dope otherwise (e.g. BPhen, Alq3).

However, the use of low work function metals has several disadvantages. It is well known that the metals can easily diffuse through the semiconductor, eventually arriving at the optically active layer quenching the excitons, thereby lowering the efficiency of the device and the lifetime. Another disadvantage is their high susceptibility to oxidation upon exposure to air. Therefore, devices using such metals as dopants, injection or cathode material require rigorous exclusion of air during production and rigorous encapsulation afterwards. Another well known disadvantage is that higher molar doping concentration of the dopant exceeding 10 mol. % may increase the undesired absorption of light in the transport layers. Yet another problem is high volatility of many simple redox dopants like Cs, leading to cross-contamination in the device assembling process making their use in device fabrication tools less attractive.

Another approach to replace metals as n-dopants and/or injection materials for ETM is the use of compounds with strong donor properties, such as tetrakis(1,3,4,6,7,8-hexahydro-2H-pyrimido[1,2-a]pyrimidinato)ditungsten (II) (W2(hpp)4) or Co(Cp*)2 (US2009/0212280, WO2003/088271) which have similar or slightly less doping/injecting ability in comparison with alkaline earth metals. Due to their still high enough electron donating capability, they are also undergoing rapid decay upon exposure to air, making their handling in device production difficult.

It is also known to mix metal organic complexes such as lithium quinolate (LiQ) into an electron transport layer to improve the device, however the exact mechanism of improvement is not well known. Investigations have shown that the use of LiQ still leads to OLEDs with high operating voltage.

Therefore, it is very desirable to provide materials which possess high doping/charge injection capability allowing for highly efficient organic electronic devices substantially preserving the long-term stability of the device and which are infinitely stable in air.

It is therefore an objective of the present invention to provide an organic electronic device, which overcomes state of the art limitations mentioned above and have improved performance compared to electronic devices of the prior art. It is especially an object, to provide an organic electronic device having reduced operating voltage and longer life time reflecting into higher power efficiency.

BRIEF SUMMARY

The object is achieved by an organic electronic device, comprising a first electrode, a second electrode, and a substantially organic layer comprising a compound according to formula (I) between the first and the second electrode:

Formula (I)

wherein $A^1$ is a C6-C20 arylene and each of $A^2$-$A^3$ is independently selected from a C6-C20 aryl, wherein the aryl or arylene may be unsubstituted or substituted with groups comprising C and H or with a further LiO group, provided that the given C count in an aryl or arylene group includes also all substituents present on the said group.

DETAILED DESCRIPTION

It is to be understood that the term substituted or unsubstituted arylene stands for a divalent radical derived from substituted or unsubstituted arene, wherein the both adjacent structural moieties (in formula (I), the OLi group and the diaryl prosphine oxide group) are attached directly to an aromatic ring of the arylene group. Examples of simple arylenes are o-, m- and p-phenylene; polycyclic arylenes may have their adjacent groups attached either on the same aromatic ring or on two different aromatic rings.

In case of arylenes derived from the polycyclic arenes, the definition of o-, m- and p-substitution is generalized as follows. As o-arylenes are understood solely those arylenes wherein the adjacent substituents in formula (I) are attached to two carbon atoms directly attached in the same aromatic ring. As p-arylenes, are generalized all arylenes having the adjacent substituents attached to the opposite sides of a rigid arene structure so that the bonds to these substituents are parallel, whereas in m-arylenes, the angle between the bonds attaching the adjacent OLi and diary1 phosphine oxide moieties is different from 180° (in the rigid arene structures) or variable, e.g. in arylenes consisting of two or more rigid arylene substructures bound together by single bonds.

Examples of generalized p-arylenes are naphthalene-1,4-diyl, naphthalene-1,5-diyl, naphthalene-2,6-diyl, 1,1'-biphenyl-4,4'-diyl. Examples of generalized m-arylenes are naphthalene-1,3-diyl, naphthalene-1,6-diyl, naphthalene-1,7-diyl, naphthalene-1,8-diyl, naphthalene-2,7-diyl, 1,1'-biphenyl-3,4'-diyl, 1,1'-biphenyl-2,4'-diyl, 1,1'-biphenyl-2,4'-diyl, 1,1'-biphenyl-2,3'-diyl, 1,1'-biphenyl-3,3'-diyl, 1,1'-biphenyl-2,2'-diyl.

Preferably, A1 is C6-C12 arylene. Even preferably, each of A2-A3 is independently selected from a C6-C 10 aryl. More preferably, both A2 and A3 are phenyls. Most preferably, A1 is o- or p-phenylene.

Preferably, A1 is C6-C12 arylene. Even preferably, each of A2-A3 is independently selected from a C6-C10 aryl. More preferably, both A2 and A3 are phenyls. Most preferably, A1 is o- or p-phenylene.

In one preferred embodiment the substantially organic layer comprises an electron transport matrix compound.

In a further preferred embodiment the electron transport matrix comprises an imidazole or a P=O functional group.

Moreover, the compound according to formula (I) and the electron transport matrix compound are preferably present in the substantially organic layer in the form of a homogeneous mixture.

Furthermore, the organic electronic device may be selected from an organic light emitting diode, organic solar cell and organic field effect transistor.

Preferred is an organic electronic device wherein the device is an organic light emitting diode with the first electrode being an anode, the second electrode being a cathode, and the device further comprising a light emitting layer between the anode and the cathode and wherein the substantially organic layer is comprised between the cathode and the light emitting layer. Alternatively or in addition, the light emitting layer of the organic electronic device comprises a light emitting polymer.

Preferably is finally the use of a material according to formula (I) in an organic electronic device, especially as a dopant in and/or adjacent an electron transport layer of the device.

The object of the present invention is also achieved by compound according to formula (I)

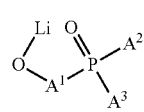

Formula (I)

wherein $A^1$ is m- or p-arylene and each of $A^2$-$A^3$ is independently selected from a C6-C20 aryl, wherein the aryl or arylene may be unsubstituted or substituted with groups comprising C and H or with a further LiO group, provided that the given C count in an aryl or arylene group includes also all substituents present on the said group.

Preferably, each of A2-A3 is independently selected from a C6-C10 aryl. More preferably, the arylene is m- or p-phenylene. Also preferably, both A2 and A3 are phenyls. Most preferably, the arylene is m-phenylene.

Other embodiments are disclosed in the subclaims.

Preferred Uses

Preferably the compound according to formula (I) is used in transport and/or injection layers, more preferably in an electron transport layer and/or electron injection layer.

The chemical compounds according to formula (I) are air-stable and capable to be evaporated without decomposition. They are also soluble in a variety of solvents. This makes the compounds according to formula (I) particularly easy to use in manufacturing processes.

The inventive organic electronic device preferably comprises a layered structure including a substrate, an anode and a cathode, the at least one substantially organic layer being disposed within the layered structure between the anode and the cathode.

The substantially organic layer may further comprise an electron transport matrix compound. The electron transport material constitutes preferably 10 weight % or more of the substantially organic layer. This is to allow charge transport through the layer. More preferred is 40 wt % or more. For an electron transport layer, it is more preferred that the electron transport matrix is the main component of the layer.

As matrix materials for electron transport layers, use may be made for example of fullerenes, such as for example C60, oxadiazole derivatives, such as for example 2-(4-biphenyl)-5-(4-tert-butylphenyl)-1,3,4-oxadiazole, quinoline-based compounds such as for example bis(phenylquinoxalines), or oligothiophenes, perylene derivatives, such as e.g. perylenetetracarboxylic acid dianhydride, naphthalene derivatives such as e.g. naphthalenetetracarboxylic acid dianhydride, or other similar compounds known as matrices in electron transport materials.

It is preferred that the electron transport material comprises a phosphine oxide or imidazole functional groups.

Compounds well suitable as electron transport materials are compounds from:

US2007/0138950, preferentially, compounds (1) and (2) on page 22, compounds (3), (4), (5), (6), and (7) on page 23, compounds (8), (9), and (10) on page 25, and compounds (11), (12), (13), and (14) on page 26, which compounds are incorporated herein by reference;

US2009/0278115 A1, preferentially, compounds (1) and (2) on page 18, which compounds are incorporated herein by reference;

compounds from US2007/0018154, preferentially the compounds of claim 10, formula 1-1, 1-2, 1-3, 1-4, 1-5, 1-6 on page 19, 1-7 to 1-146 on pages 20 to 26. Compounds from US2008/0284325 A1, preferentially compounds on page 4: 2-(4-(9,10-diphenylanthracen-2-yl)phenyl)-1-phenyl-1H-benzo[d]imidazole, 2-(4-(9,10-di([1,1'-biphenyl]-2-yl)anthracen-2-yl)phenyl)-1-phenyl-1H-benzo[d]imidazole, 2-(4-(9,10-di(naphthalen-1-yl)anthracen-2-yl)phenyl)-1-phenyl-1H-benzo[d]imidazole, 2-(4-(9,10-di(naphthalen-2-yl)anthracen-2-yl)phenyl)-1-phenyl-1H-benzo[d]imidazole, 2-(4-(9,10-di([1,1':3',1''-terphenyl]-5'-yl)anthracen-2-yl)phenyl)-1-phenyl-1H-benzo[d]imidazole, and the compound on page 5, which compounds are incorporated herein by reference;

naphthacene derivatives from US2007/0222373, preferentially, compounds (A-1) and (A-2) from page 17, compounds (A-3) from page 18 and (A-4) from page 19, which compounds are incorporated herein by reference;

compounds from US2008/0111473, preferentially, compound 1 on page 61, compound 2 on page 62, compounds 3 and 4 on page 63, compound 5 on page 64, and compound 6 on page 65, which compounds are incorporated herein by reference;

compound H-4 from page 20, and compounds (1) and (2) of page 12 of US2010/0157131, which compounds are incorporated herein by reference;

compounds from US2010/0123390, according to general formula (1), preferentially, compounds H4, H5 p. 21, H7 p. 22, H11, H12, H13 p. 23, H16, and H18 p. 24, which compounds are incorporated herein by reference;

US2007/0267970, preferentially 2-([1,1'-biphenyl]-4-yl)-1-(4-(10-(naphthalen-2-yl)anthracen-9-yl)phenyl)-2,7a-dihydro-1H-benzo[d]imidazole (compound 1), 2-([1,1'-biphenyl]-2-yl)-1-(4-(10-(naphthalen-2-yl)anthracen-9-yl)phenyl)-2,7a-dihydro-1H-benzo[d]imidazole (compound 2). Compound (C-1) from US2007/0196688, p. 18, which is incorporated herein by reference;

Other suitable compounds are 7-(4'-(1-phenyl-1H-benzo[d]imidazol-2-yl)-[1,1'-biphenyl]-4-yl)dibenzo[c,h]acridine (ETM1), (4-(dibenzo[c,h]acridin-7-yl)phenyl)diphenylphosphine oxide (ETM2), 7-(4-(1-phenyl-1H-benzo[d]imidazol-2-yl)phenyl)dibenzo[c,h]acridine (ETM5).

Suitable hole transport materials (HTM) can be, for instance HTM from the diamine class, where a conjugated system is provided at least between the two diamine nitrogens. Examples are N4,N4'-di(naphthalen-1-yl)-N4,N4'-diphenyl-[1,1'-biphenyl]-4,4'-diamine (HTM1), N4,N4, N4", N4"-tetra([1,1'-biphenyl]-4-yl)-[1,1':4',1"-terphenyl]-4,4"-diamine (HTM2). The synthesis of diamines is well described in literature; many diamine HTMs are readily commercially available.

It will be understood that the aforementioned matrix materials may also be used in a mixture with one another or with other materials in the context of the invention. It will be understood that use may also be made of suitable other organic matrix materials which have semiconductive properties.

In another preferred embodiment, the substantially organic layer is present in a pn junction, the pn junction having at least two layers, namely a p- and n-layer, and optionally an interlayer i in between, wherein the interlayer i and/or the n-layer is (are) the substantially organic semiconducting layer.

The organic electronic device may additionally comprise a polymer semiconducting layer.

Most preferably, the organic electronic device is a solar cell or a light emitting diode.

The organic electronic device may be also a field effect transistor comprising a semiconducting channel, a source electrode, and a drain electrode, the substantially organic layer being provided in between the semiconducting channel and at least one of the source electrode and the drain electrode.

In a further most preferred embodiment, the substantially organic layer comprising the chemical compound according to formula (I) is an electron injection layer and/or an electron transport layer.

Any layers of the inventive organic electronic device, especially the substantially organic layer can be deposited by known techniques, such as vacuum thermal evaporation (VTE), organic vapour phase deposition, laser induced thermal transfer, spin coating, blade or slit coating, inkjet printing, etc. A preferred method for preparing the organic electronic device according to the invention is vacuum thermal evaporation.

Surprisingly, it was found that the inventive organic electronic device overcomes disadvantages of prior art devices and has in particular an improved performance compared to electronic devices of the prior art, for example with regard to efficiency.

Injection Layer

In a preferred embodiment, the substantially organic layer, having the compound according to formula (I) as its main component, is adjacent to a cathode, preferably between a cathode and one of an ETL (electron transporting layer) or HBL (hole blocking layer). The present invention has the advantages that, especially for non-inverted structures, the simplest form is also the one with a significantly improved performance compared to the structure not using an injection layer. The compound according to formula (I) can be used as a pure layer and is then preferably the only layer between an electron transporting layer (ETL or HBL) and the cathode. In this regard for an OLED the EML (emitter layer) and ETL matrix can be the same if the emission zone is far from the cathode. In another embodiment, the ETL and the EML are layers of different composition, preferably of a different matrix.

Such a pure layer as injection layer in organic electronic devices has a preferable thickness between 0.5 nm and 5 nm.

The thickness of the layer comprising the compound according to formula (I) is the nominal thickness, such thickness is usually calculated from the mass deposited on a certain area by the knowledge of the material's density. For example, with vacuum thermal evaporation VTE, the nominal thickness is the value indicated by the thickness monitor equipment. In reality, since the layer is not homogeneous and not flat at least at one interface, its final thickness is difficult to measure, in this case, the average value can be used. The cathode in this regard is a conductive layer having optionally any surface modifications to modify its electrical properties, e.g. to improve its work-function or conductivity. Preferably, the cathode is a double layer, more preferably it is a single layer to avoid complexity.

Semiconducting Layer

It is even preferred that the organic layer is an electron transport layer adjacent to the cathode and comprising the compound according to formula (I). If the ETL is directly adjacent to the cathode, this simplification has the advantage that no additional injection layer is required. Alternatively, an additional injection layer can be provided between the ETL and the cathode. This additional layer can be a layer having the chemical compound according to formula (I) as its main component, as already illustrated above. In one even preferred embodiment, the ETL is beneath the cathode (no other layer in between) wherein the cathode is the top electrode, which is formed after forming the ETL (non-inverted structure).

For an OLED the EML (emitter layer) and ETL matrix can be the same if the emission zone is far from the cathode. In another embodiment, the ETL and the EML are layers of different composition, preferably of a different matrix.

Advantages of the Invention

Surprisingly, it was observed an improvement of the OLED lifetime, and a lowering of the operating voltage.

Polymer Hybrid OLED or Solar Cell

In a further preferred embodiment the substantially organic layer comprising the chemical compound according to formula (I) is used in combination with a polymer semiconductor, preferably between a cathode and a polymer layer, wherein the polymer layer preferably comprises the optoelectronic active region of the device (emitting region of an OLED or the absorbing region of a solar cell). All alternatives of layers comprising the chemical compound according to formula (I) or being composed thereof can be used in combination with that polymer layer. Exemplary alternative layers can be an injection layer being composed of the chemical compound according to formula (I), an injection layer comprising the chemical compound and a metal, an electron transport layer having the chemical compound with or without a metal. The electronic interface to the cathode is then strongly improved given the high electron injection capability of the chemical compound (I).

Electrical Doping

The invention can be used as an alternative to conventional doping of organic semiconducting layers. By using the term doping it is meant electrical doping as explained above. This doping can also be called redox-doping or charge transfer doping. It is known that the doping increases the density of charge carriers of a semiconducting matrix towards the charge carrier density of the undoped matrix. An electrically doped semiconductor layer also has an increased effective mobility in comparison with the undoped semiconductor matrix.

US2008227979 discloses in detail the doping of organic transport materials, also called ma-trix, with inorganic and with organic dopants. Basically, an effective electronic transfer occurs from the dopant to the matrix increasing the Fermi level of the matrix. For an efficient trans-fer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than +0.3 eV.

Typical examples of doped hole transport materials are: copperphthalocyanine (CuPc), which HOMO level is approximately −5.2 eV, doped with tetrafluoro-tetracyano-quinonedimethane (F4TCNQ), which LUMO level is about −5.2 eV; zincphthalocyanine (ZnPc) (HOMO=−5.2 eV) doped with F4TCNQ; a-NPD (N,N'-Bis(naphthalen-1-yl)-N,N-bis(phenyl)-benzidine) doped with F4TCNQ.

One of the preferred modes of the invention is an OLED with the hole transporting side of OLED comprising a p-dopant and the electron transporting side comprising the material according to Formula (I). For example: an OLED with a p-doped HTL and an ETL with a ETM and the material according to Formula (I).

ORGANIC ELECTRONIC DEVICES

Figure 1:
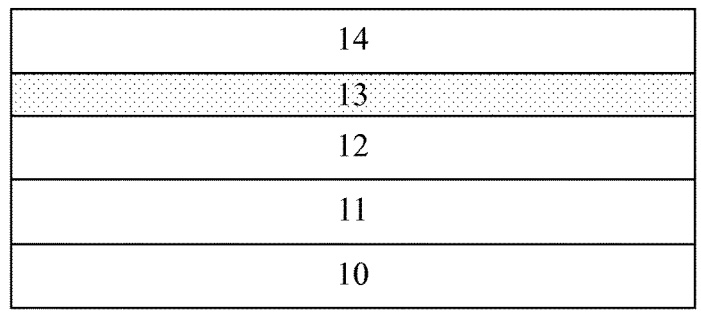
FIG. 1 illustrates a first embodiment of an inventive organic electronic device.

FIG. 1 illustrates a first embodiment of an inventive organic electronic device in the form of a stack of layers forming an OLED or a solar cell. In FIG. 1, 10 is a substrate, 11 is an anode, 12 is an EML or an absorbing layer, 13 is a EIL (electron injection layer), 14 is a cathode.

The layer 13 can be a pure layer of a compound according to formula (1). At least one of the anode and cathode is at least semi-transparent. Inverted structures are also foreseen (not illustrated), wherein the cathode is on the substrate (cathode closer to the substrate than the anode and the order of the layers 11-14 is reversed). The stack may comprise additional layers, such as ETL, HTL, etc.

Figure 2:
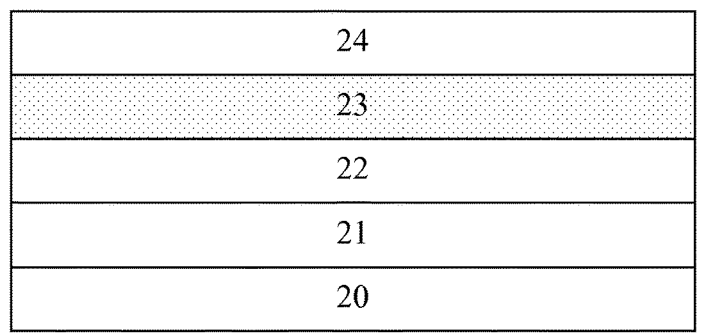
FIG. 2 illustrates a second embodiment of an inventive organic electronic device.

FIG. 2 represents a second embodiment of the inventive organic electronic device in the form of a stack of layers forming an OLED or a solar cell. Here, 20 is a substrate, 21 is an anode, 22 is an EML or an absorbing layer, 23 is an ETL, 24 is a cathode. The layer 23 comprises an electron transport matrix material and a compound according to formula (I).

Figure 3:
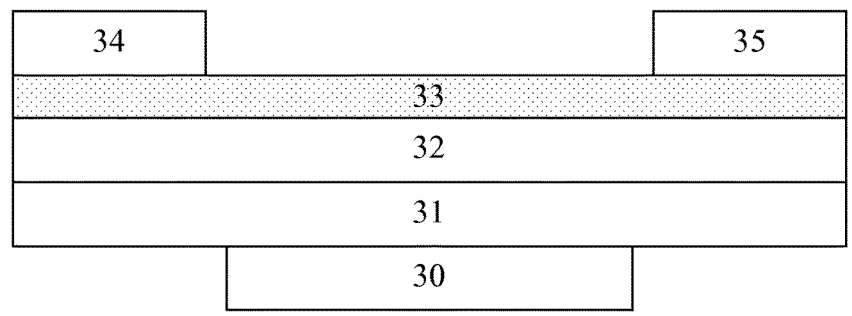
FIG. 3 shows a third embodiment of an inventive organic electronic device.

FIG. 3 illustrates a third embodiment of the inventive device in the form of an OTFT, with semi-conductor layer 32, a source electrode 34 and a drain electrode 35. An unpatterned (unpatterned between the source and drain electrodes) injection layer 33 provides charge carrier injection and extraction between the source-drain electrodes and semi-conducting layer. OTFT also comprises a gate insulator 31 (which could be on the same side as the source drain electrodes) and a gate electrode 30, which gate electrode 30 is on the side of the layer 31 which is not in contact with the layer 32. Obviously, the whole stack could be inverted. A substrate may also be provided. Alternatively, insulator layer 31 may be the substrate.

EXAMPLES

Compounds used as electron transporting matrices for testing the effects of inventive compounds

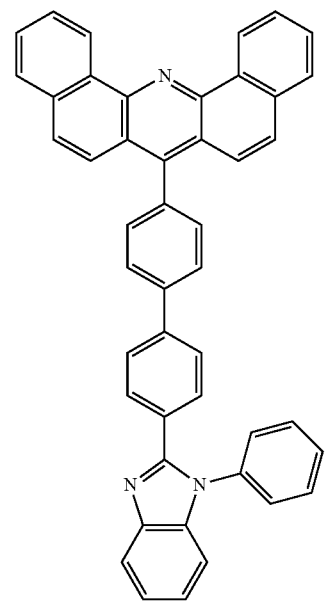

ETM1

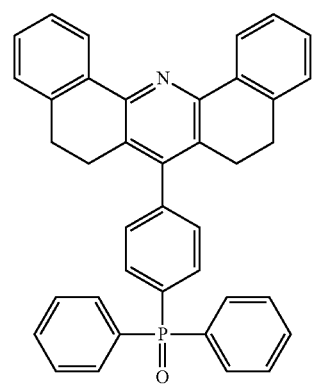

ETM2

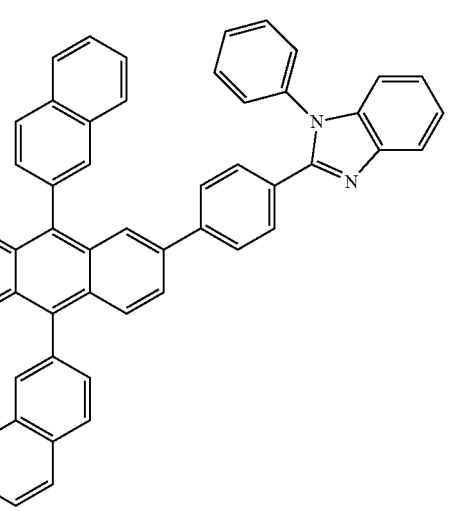

ETM3

ETM1 and ETM2 were described in patent application WO2011/154131 (Examples 4 and 6), ETM3 (CAS number 561064-11-7) is commercially available. ETM4 was synthesized from the intermediate (10) described in Example 3 of WO2011/154131 according to following procedure:

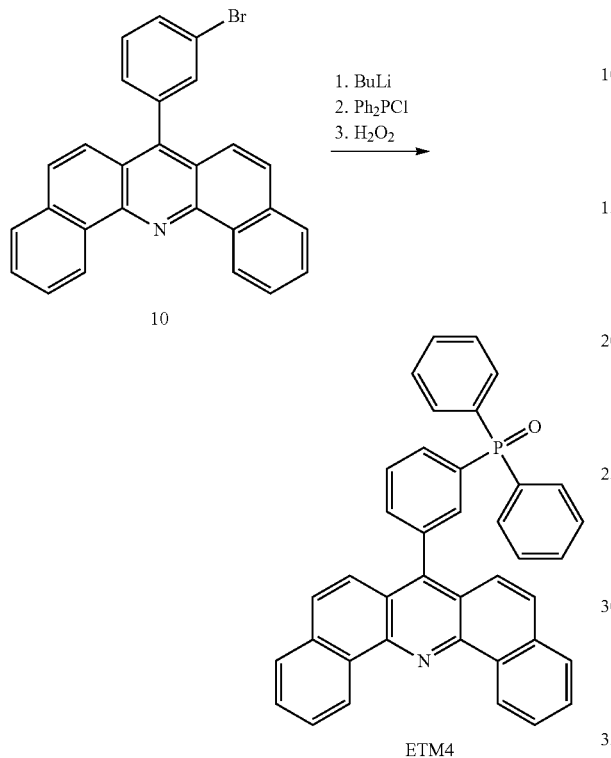

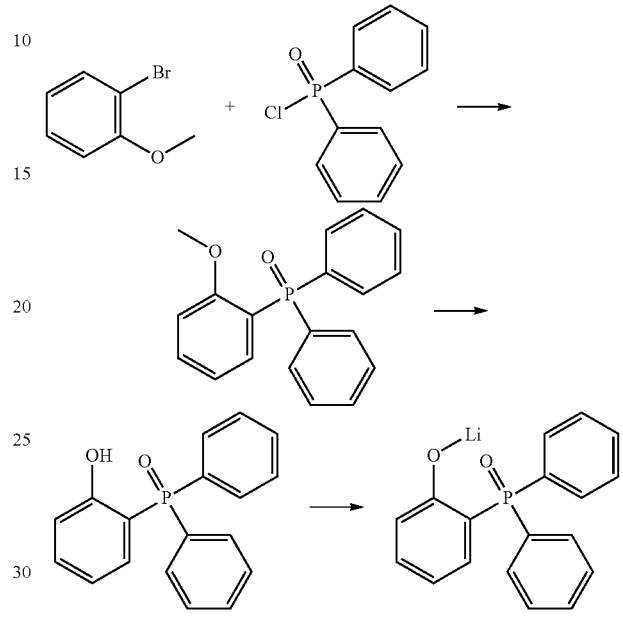

(10) (4.06 g, 9.35 mmol) was dissolved in 60 mL dry THF under argon. The solution was cooled down to −78° C., n-butyllithium was added dropwise within 25 min (2.5 mol/L, 5.6 mL, 14.0 mmol), and the reaction mixture stirred at that temperature for half an hour. The temperature was then let rise up to −50° C., and diphenylphosphine chloride (2.17 g, 9.82 mmol) was added. The mixture was stirred overnight at room temperature. The reaction was then quenched with methanol (MeOH, 30 mL), and the solvents were evaporated. The solid residue was dissolved in 50 mL dichloromethane (DCM), 8 mL aqueous $H_2O_2$ (30% by weight) was then added and the mixture was stirred for 24 hours. The reaction mixture was then washed with 50 mL brine and 2×50 mL water, the organic phase was dried and evaporated. The crude product was purified via column chromatography ($SiO_2$, DCM, then DCM/MeOH 99:1). The obtained foamy product was then washed two times with 40 mL acetonitrile.

Yield: 3.1 g (60%). Pale yellow solid.
NMR: $^{31}P$ NMR ($CDCl_3$, 121.5 MHz): δ (ppm): 27 (in) $^1H$ NMR (500 MHz, $CD_2Cl_2$) δ (ppm): 9.78 (d, 8.03 Hz, 2H), 7.95 (m, 3H), 7.85 (m, 2H), 7.76 (m, 11H), 7.57 (ddd, 1.39 Hz, 9.84 Hz, 7.24 Hz, 2H), 7.50 (m, 6H).
m.p. 250° C. (from differential scanning calorimetry (DSC) peak).

Synthetic Procedure for Preparing the Compounds of Formula (I)

All reactions were performed under inert atmosphere. Commercial reactants and reagents were used without further purification. Reaction solvents tetrahydrofurane (THF), acetonitrile (AcN) and dichloromethane (DCM) were dried by a solvent purification system (SPS).

1) Synthetic Scheme for the Synthesis of Lithium 2-(diphenylphosphoryl)phenolate (1)

1.1) (2-methoxyphenyl)diphenylphosphine oxide

A solution of 3.36 mL (5.0 g, 26.7 mmol, 1.05 eq.) o-bromoanisole in 20 mL dry THF from SPS was slowly added to a suspension of magnesium turnings (0.98 g, 40.1 mmol, 1.57 eq.) in 20 mL THF, in presence of a catalytic amount of elemental iodine. After the initial temperature rise was over, the reaction mixture was refluxed for 2 h, then let return to room temperature and inert filtered. The filtrate was cooled at −50° C. and a solution of 6 g (25.4 mmol, 1 eq.) of diphenylphosphinyl chloride in 20 mL THF was added drop wise. The suspension was allowed to warm slowly to room temperature and stirred overnight. The mixture was then refluxed for 3 h, and then cooled down to room temperature. The reaction was quenched by the addition of 10 mL methanol. The solvents were evaporated under vacuum, the residue was suspended in 50 mL chloroform and filtered. The filtrate was evaporated to afford (2-methoxyphenyl)diphenylphosphine oxide quantitatively (7.8 g, 25.4 mmol). The crude product was used without further purification.

GC-MS: m/z=308 (96% purity)

1.2) (2-hydroxyphenyl)diphenylphosphine oxide

A solution of 7.8 g (25.4 mmol, 1 eq.) (2-methoxyphenyl) diphenylphosphine oxide in 20 mL dry DCM was cooled to −5° C. To the reaction mixture, 28 mL (1.1 eq.) of a 1M boron tribromide solution in DCM were slowly added. The cooling bath was removed and the reaction was stirred at room temperature overnight. After quenching with 10 mL methanol, the mixture was neutralized with a saturated aqueous sodium hydrogen carbonate solution. Extraction from this mixture with 50 mL chloroform followed by evaporation and precipitation from chloroform with hexane afforded 4.1 g (13.9 mmol, 55% yield) (2-hydroxyphenyl)diphenylphosphine oxide.

HPLC purity: 97% (UV detector at 300 nm)

1.3) Lithium 2-(diphenylphosphoryl)phenolate (1)

To 4.0 g (13.6 mmol, 1eq.) of (2-hydroxyphenyl)diphenylphosphine oxide suspended in 80 mL dry AcN 109 mg (13.6 mmol, 1 eq.) lithium hydride was added under argon stream. The suspension was stirred overnight at room temperature, then filtered and washed with AcN to afford 3.40 g (83% yield) of a grey powder. Further purification was achieved by gradient sublimation.

HPLC: 97% (250 nm), 98% (300 nm)

DSC: melting point: 436° C. (onset)

$^{1}$H-NMR (CD$_3$OD, 500.13 MHz): δ[ppm]=6.38 (broad s, 1H), 6.65 (m, 1H), 6.77 (broad s, 1H), 7.18 (t, J=8 Hz, 1H), 7.42 (td, J=3 Hz and 8 Hz, 4H), 7.50 (m, 2H), 7.65 (in, 4H).

$^{13}$C-NMR (CD$_3$OD, 125.76 MHz, with P—C coupling): δ[ppm]=114.01 (d, J=11 Hz), 115.80 (d, J=3 Hz), 122.19 (d, J=10 Hz), 129.35 (d, J=12 Hz), 132.69 (d, J=15 Hz), 133.34 (d, J=105 Hz), 134.34 (s), 134.64 (d, J=10 Hz), 135.19 (s), 135.73 (d, J=3 Hz).

$^{31}$P-NMR (CD$_3$OD, 125.76 MHz, without P—C coupling): δ[ppm]=37.28.

2) Synthetic Scheme for the Synthesis of Lithium 3-(diphenylphosphoryl)phenolate (2)

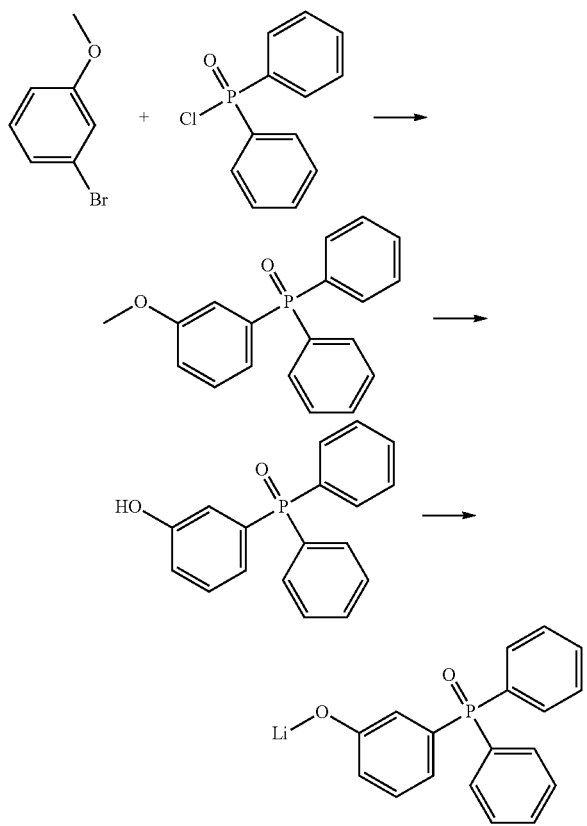

2.1) (3-methoxyphenyl)diphenylphosphine oxide

A solution of 3.36 mL (5.0 g, 26.7 mmol, 1.05 eq.) of 3-bromoanisole in 20 mL dry THF from SPS was slowly added to a suspension of magnesium turnings (0.98 g, 40.1 mmol, 1.57 eq.) in 20 mL THF, in presence of a catalytic amount of elemental iodine. After the initial temperature rise was over, reaction mixture was refluxed 2 h, then let return to room temperature and inert filtered. The filtrate was cooled at −50° C. and a solution of 6 g (25.4 mmol, 1 eq.) diphenylphosphinyl chloride in 20 mL THF was added drop wise. The suspension was allowed to warm slowly to room temperature and stirred overnight. The mixture was then refluxed for 3 h, and then cooled down to room temperature. The reaction was quenched by the addition of 10 mL methanol. The solvents were evaporated under vacuum and the residue was suspended in 50 mL chloroform and filtered. The filtrate was evaporated to afford (3-methoxyphenyl)diphenylphosphine oxide quantitatively (7.8 g, 25.4 mmol). The crude product was used without further purification.

GC-MS: m/z=308 (96%)

2.2) (3-hydroxyphenyl)diphenylphosphine oxide

A solution of 7.8 g (25.4 mmol, 1 eq.) (3-methoxyphenyl)diphenylphosphine oxide in 20 mL dry DCM was cooled to −5° C. To the reaction mixture were slowly added 28 mL (1.1 eq.) of a 1M solution of boron tribromide in DCM. The cooling bath was removed and the reaction was stirred at room temperature overnight. After quenching with 10 mL methanol, the mixture was neutralized with a saturated aqueous sodium hydrogen carbonate solution. Extraction from this mixture with 50 mL chloroform followed by evaporation and precipitation from chloroform with hexane afforded 4.1 g (13.9 mmol, 55% yield) (3-hydroxyphenyl)diphenylphosphine oxide.

HPLC: 96% (300 nm)

2.3) Lithium 3-(diphenylphosphoryl)phenolate (2)

To a suspension of 4.0 g (13.6 mmol, 1 eq.) of (3-hydroxyphenyl)diphenylphosphine oxide in 80 mL dry can, 109 mg (13.6 mmol, 1eq.) of lithium hydride was added under argon stream. The suspension was stirred overnight at room temperature, then filtered and the solid product washed with AcN to afford 3.40 g (83% yield) of a grey powder. Further purification was achieved by gradient sublimation.

HPLC: 97% (250 nm), 98% (300 nm)

DSC: melting point: 177° C. (onset)

$^{1}$H-NMR (CD$_3$OD, 500.13 MHz): δ[ppm]=7.02-7.07 (m, 3H, Ar—H from phenolic ring), 7.34-7.38 (m, 1H, Ar—H from phenolic ring), 7.54-7.56 (in, 4H, Ar—H phenyl rings), 7.61-7.65 (m, 6H, Ar—H from phenyl rings).

$^{13}$C-NMR (CD$_3$OD, 125.76 MHz, with P—C coupling): δ[ppm]=119.69 (d, J=11 Hz), 121.02 (d, J=3 Hz), 124.15 (d, J=10 Hz), 130.13 (d, J=12 Hz), 131.48 (d, J=15 Hz), 132.93 (d, J=105 Hz), 133.27 (d, J=10 Hz), 133.89 (d, J=105 Hz), 133.91 (d, J=3 Hz), 159.33 (d, J=15 Hz).

$^{31}$P-NMR (CD$_3$OD, 125.76 MHz, without P—C coupling): δ[ppm]=32.83.

3) Lithium 2,2'-(phenylphosphoryl)diphenolate (3)

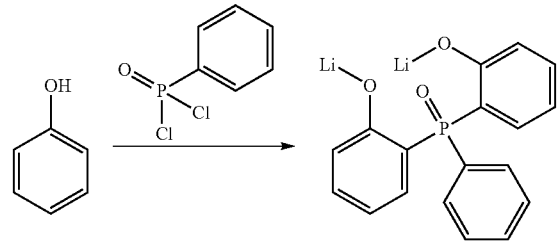

To a solution of 3.58 g (38 mmol, 2.1 eq.) phenol in 80 mL dry THF, 5.4 mL (2.1 eq.) diisopropylamine were added dropwise and the whole mixture was cooled to 0° C. 3.53 g (18 mmol, 1 eq.) dichlorophenyl phosphine oxide were added dropwise at this temperature with a syringe, leading to the formation of a white precipitate. The reaction mixture was stirred vigorously over night at room temperature. Inert filtration of this mixture afforded a clear filtrate that was added to a solution of freshly prepared lithium diisopropylamide (43 mmol, 2.4 eq.) in 100 mL dry THF cooled at −78° C. The reaction mixture was let return to room temperature over night. After evaporation of the solvents, the brown residue was dissolved in 200 mL chloroform, and precipitated by the addition of 300 mL n-hexane. A beige solid was isolated by filtration, which was further purified by a slurry wash in 150 mL AcN to afford after filtration and drying 3.6 g (62% yield) (3) as a light beige solid.

HPLC: 97% (300 nm)

$^1$H-NMR (CD$_3$OD, 500.13 MHz): δ[ppm]=6.50 (t, J=7 Hz, 2H), 6.65 (dd, J=6 Hz and 8 Hz, 2H), 7.16 (dd, J=8 Hz and 14 Hz, 2H), 7.22 (t, J=8 Hz, 2H), 7.40 (td, J=2 Hz and 8 Hz, 2H), 7.48 (td, J=1 Hz and 8 Hz, 1H), 7.56 (dd, J=8 Hz and 13 Hz, 2H).

4) Synthetic Scheme for Lithium 3-(diphenylphosphoryl)-[1,1'-biphenyl]-4-olate (4)

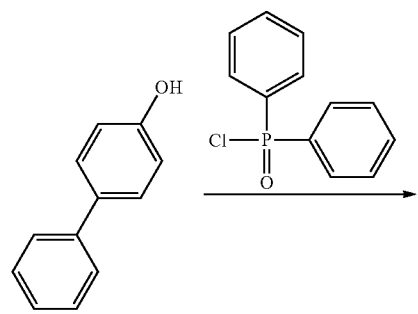

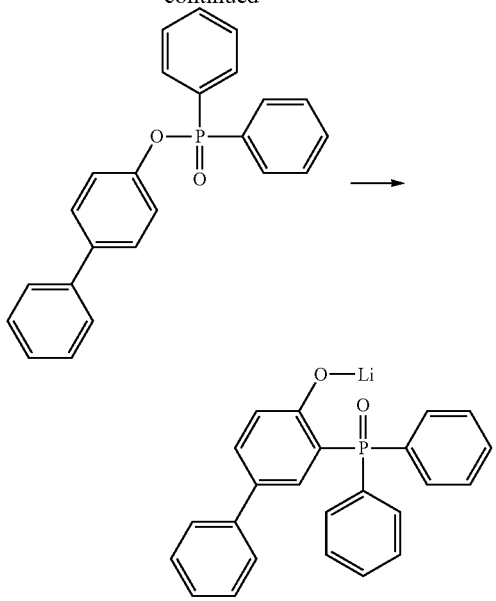

4.1) Synthesis of [1,1'-biphenyl]-4yl diphenylphosphinate

To a solution of 1.0 g (5.9 mmol, 1.1 eq.) of p-phenylphenol in 30 mL dry THF, 0.8 mL (2.1eq.) diisopropylamine were added dropwise and the whole mixture was cooled to 0° C. 1.26 g (5.3 mmol, 1eq.) chlorodiphenylphosphine oxide were added dropwise at this temperature with a syringe, leading to the formation of a white precipitate. The reaction mixture was stirred vigorously over night at room temperature. Filtration of this mixture followed by evaporation of the solvents afforded a beige powder. Obtained 960 mg (49% yield) of [1,1'-biphenyl]-4-yl diphenylphosphinate.

HPLC: 98.6% (250 nm)

4.2) Synthesis of Lithium 3-(diphenylphosphoryl)-[1,1'-biphenyl]-4-olate (4)

A solution of 0.96 g (2.6 mmol, 1.0 eq.) [1,1'-biphenyl]-4-yl diphenylphosphinate in 20 mL dry THF was added to a solution of freshly prepared lithium diisopropylamide (2.8 mmol, 1.1eq.) in 20 mL THF cooled at −78° C. The reaction mixture was let return to room temperature over night. After filtration of the salts and evaporation of the solvents, the brown residue was washed in a few mL of THF to afford after filtration and drying 560 mg (58% yield) of a light beige solid.

HPLC: 94.8% (250 nm)

$^1$H-NMR (CD$_3$OD, 500.13 MHz): δ[ppm]=6.69 (dd, J=6 Hz and 9 Hz, 1H), 7.12 (t, J=7 Hz, 1H), 7.26 (m, 2H), 7.34 (m, 4H), 7.48 (td, J=2 Hz and 8 Hz, 3H), 7.56 (m, 2H), 7.74 (m, 5H).

5) Synthetic Scheme for Lithium 4-(diphenylphosphoryl)phenolate (5)

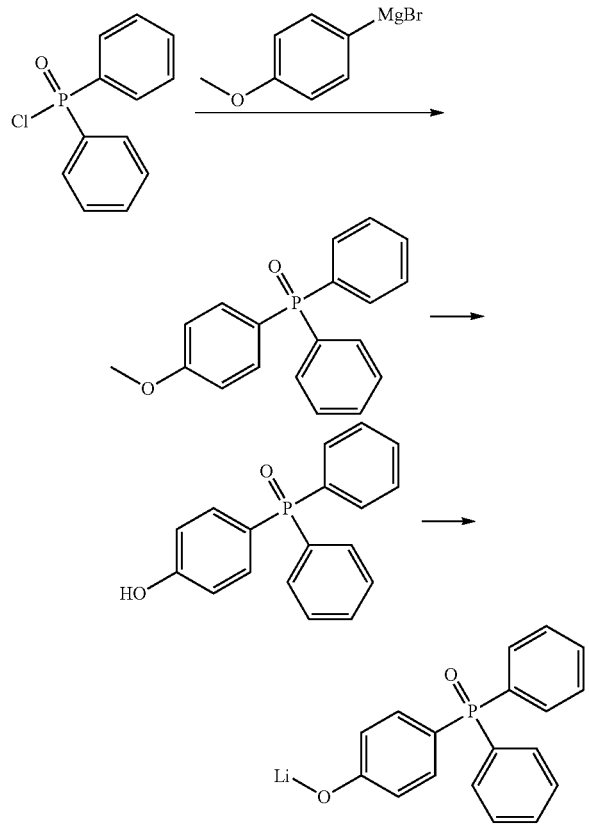

4.1) Synthesis of (4-methoxyphenyl)diphenylphosphine oxide

A solution of 3.34 mL (26.7 mmol, 1.0eq.) 4-bromoanisole in 20 mL dry THF was added dropwise to a suspension of 960 mg (40 mmol, 1.5eq.) magnesium turnings with a catalytic amount of iodine in 20 mL dry THF cooled at 0° C. After the exothermic addition was complete, reaction mixture was further refluxed for 2 h, and then the rests of magnesium were filtered off under inert conditions. To the cooled filtrate (at −50° C.), 5.1 mL (26.7 mmol, 1 eq.) chlorodiphenyl phosphine oxide were added. The reaction mixture was let return to room temperature over night. Gel filtration (SiO2, DCM/MeOH 99:1) afforded 5.66 g (67% yield) of a yellow glassy solid.

GCMS: 100% m/z 308 [M]$^+$

4.2) Synthesis of (4-hydroxyphenyl)diphenylphosphine oxide 40.9 mL (2.1 eq.) of 1.6M boron tribromide solution in dichloromethane were added dropwise to a solution of 5.6 g (18.2 mmol, 1.0 eq.) (4-methoxyphenyl)-diphenyl-phosphine oxide in 50 mL dry DCM cooled at 0° C. The reaction mixture was heated at 40° C. over night, and then quenched by a few drops of MeOH1. After one hour, the mixture was washed with an aqueous 1M sodium hydrogen carbonate solution and extracted with chloroform. The organic layer was thoroughly washed with water until the water layer was pH-neutral, and then evaporated to dryness. The residue was further slurry washed with 30 mL DCM to afford 1.23 g (23% yield) of a beige solid GCMS: 100% m/z 294 [M]$^+$

4.3) Synthesis of Lithium 4-(diphenylphosphoryl)phenolate (5)

1.23 g (42 mmol, 1 eq.) (4-hydroxyphenyl)diphenylphosphine oxide was dissolved at 40° C. in 45 mL dry DCM, then let return to room temperature. 29 mg (42 mmol, 1 eq.) lithium hydride were added to the mixture, that was again heated to 40° C. for 15 minutes, then let return to room temperature over night. After evaporation of the solvents, the residue was slurry washed with 20 mL hexane to afford 1.16 g (93%) of a light beige solid.

HPLC: 100% (300 nm)

$^1$H-NMR (THF-d8, 500.13 MHz): δ[ppm]=6.82 (dd, J=2 Hz and 9 Hz, 2H), 7.40-7.51 (m, 8H), 7.63-7.67 (m, 4H).

Alternative Procedure for the Compound (1)

Oxidation of (2-hydroxyphenyl)diphenylphosphine 32.25 g (116 mmol) (2-Hydroxyphenyl)diphenylphosphine were dissolved in 480 ml of dichloromethane and 17.8 ml of 30% aqueous hydrogen peroxide solution were added dropwise. The resulting suspension was stirred for 1.5 days at room temperature. The precipitate was filtered and washed with 30 ml of dichloromethane.

After drying 27.82 g (82% yield) of HPLC-pure (2-hydroxyphenyl) diphenylphosphine oxide were obtained.

Deprotonation of (2-hydroxyphenyl)diphenylphosphine oxide 27.82 g (94.6 mmol) of (2-hydroxyphenyl)diphenylphosphine oxide were suspended in 1.4 l of dichloromethane. 0.833 g (104.1 mmol) of lithium hydride was added and the suspension was stirred for 1.5 days before removing the solvent under reduced pressure. The crude product was stirred with 300 ml of chloroform over night and the solid was filtered, washed with chloroform and dried in vacuum. 26.46 g (93% yield) were sublimed in high vacuum for further purification.

DEVICE EXAMPLES

Comparative Example 1

A first blue emitting device was made by depositing a anode of 100 nm thick Ag on a glass substrate. A 40 nm doped layer of HTM2 (matrix to dopant weight ratio of 97:3) was subsequently deposited as hole injection and transport layer, followed by an 92 nm undoped layer of HTM2. Subsequently, an blue fluorescent emitting layer of ABH113 (Sun Fine Chemicals) doped with NUBD370 (Sun Fine Chemicals) (matrix dopant ratio of 97:3 wt %) was deposited with a thickness of 20 nm. A 36 nm layer of the compound according ETM1 was deposited on the emitting layer as ETL. A 1 nm thick layer of lithium quinolate (LiQ) followed the ETM1 layer. Subsequently a layer of Mg:Ag (90:10 wt %) with a thickness of 12 nm was deposited as transparent cathode followed by 60 nm of HTM2 as cap layer.

This device showed a voltage of 4.2 V at a current density of 10 mA/cm2, a luminance of 122 cd/m2 at a current density of 10 mA/cm2 with a current efficiency of 1.2 cd/A at the same current density.

In the whole stack HTM2 can be replaced by HTM1 with similar results.

Comparative Example 2

A similar device was produced as in Comparative Example 1, with the difference that the ETL was deposited as a 36 nm thick layer of a mixture between the ETM1 and LiQ with a weight ratio of 1:1.

This device showed a voltage of 4.0 V at a current density of 10 mA/cm2, a luminance of 260 cd/m2 at a current density of 10 mA/cm2 with a current efficiency of 2.6 cd/A at the same current density.

Inventive Example 1

A similar device was produced as in Comparative Example 1, with the difference that the ETL was deposited as a 36 nm thick layer of a mixture between the compound according to Formula (I) and ETM1 with a weight ratio of 1:1.

This device showed a slightly increased voltage of 4.3 V at a current density of 10 mA/cm2, an extremely enhanced luminance of 532 cd/m2 at a current density of 10 mA/cm2 with a current efficiency of 5.3 cd/A at the same current density. These values are remarkable good for a blue emitting OLED. Given the high performance, it is possible to operate an OLED with same or higher light intensity than the OLEDs of the comparative examples at a lower voltage.

OLEDs with other ETMs and the compound according to Formula (I) showed similar performance improvements OLEDs with other ETMs and the compound according to Formula (I) showed similar performance improvements, as shows the Table 1:

| compound | ETL matrix | Voltage (V) at 10 mA/cm² | CIE 1931 x | CIE 1931 y | QEff (%) at 10 mA/cm² |
|---|---|---|---|---|---|
| 1 | 3 | 4.0 | 0.14 | 0.09 | 6.0 |
| 1 | 2 | 4.6 | 0.14 | 0.09 | 5.5 |
| 2 | 3 | 7.3 | 0.14 | 0.09 | 2.7 |
| 2 | 2 | 8.3 | 0.14 | 0.10 | 5.0 |
| LiQ | 3 | 4.3 | 0.13 | 0.11 | 5.1 |
| LiQ | 2 | 4.9 | 0.13 | 0.10 | 3.8 |

These results show that the inventive devices comprising compounds of formula (I) are not only useful alternatives to the devices using known LiQ as an electron-injecting additive. Use of compounds of formula (I) significantly broadens the offer of electron transport improving additives, allowing improving and optimizing device performance beyond limits known in the art.

The features disclosed in the foregoing description, the claims and in the drawings may both separately and in any combination thereof, be material for realising the invention in diverse forms thereof.

The invention claimed is:

1. An organic electronic device, comprising a first electrode, a second electrode, and a substantially organic layer arranged between the first electrode and the second electrode, the substantially organic layer comprising a compound according to formula (I):

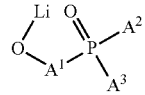

Formula (I)

wherein $A^1$ is a $C_6$-$C_{20}$ arylene, and each of $A^2$-$A^3$ is independently selected from a $C_6$-$C_{20}$ aryl, wherein the aryl or arylene is unsubstituted or substituted with groups comprising C and H or with a further LiO group, wherein the $C_6$-$C_{20}$ carbons of the aryl or arylene groups includes all substituents present on the aryl or arylene groups.

2. The organic electronic device according to claim 1, wherein $A^1$ is a $C_6$-$C_{12}$ arylene.

3. The organic electronic device according to claim 1, wherein each of $A^2$-$A^3$ is independently selected from a $C_6$-$C_{10}$ aryl.

4. The organic electronic device according to claim 1, wherein $A^2$ and $A^3$ are phenyl.

5. The organic electronic device according to claim 1, wherein $A^1$ is o- or p-phenylene.

6. The organic electronic device according to claim 1, wherein the substantially organic layer comprises an electron transport matrix compound.

7. The organic electronic device according to claim 6, wherein the electron transport matrix compound comprises an imidazole or a P═O functional group.

8. The organic-electronic device according to claim 6, wherein the compound according to formula (I) and the electron transport matrix compound are present in the substantially organic layer as a homogeneous mixture.

9. The organic electronic device according to claim 1, wherein the device is selected from an organic light emitting diode, organic solar cell, or organic field effect transistor.

10. The organic electronic device according to claim 9, wherein the device is an organic light emitting diode, wherein the first electrode is an anode, the second electrode is a cathode, and the device further comprises a light emitting layer arranged between the anode and the cathode, and wherein the substantially organic layer is arranged between the cathode and the light emitting layer.

11. The organic electronic device according to claim 10, wherein the light emitting layer comprises a light emitting polymer.

* * * * *